(12) United States Patent
Heidelbaugh et al.

(10) Patent No.: US 7,683,089 B1
(45) Date of Patent: Mar. 23, 2010

(54) 4-(PHENYLMETHYL AND SUBSTITUTED PHENYLMETHYL)-IMIDAZOLE-2-THIONES ACTING AS SPECIFIC ALPHA2 ADRENERGIC AGONISTS

(75) Inventors: Todd M. Heidelbaugh, Fountain Valley, CA (US); Ken Chow, Newport Coast, CA (US); Phong X. Nguyen, Placentia, CA (US); Daniel W. Gil, Corona Del Mar, CA (US); John E. Donello, Dana Point, CA (US); Michael E. Garst, Newport Beach, CA (US); Larry A. Wheeler, Irvine, CA (US)

(73) Assignee: Allergan, Inc, Irvine, CA (US)

( * ) Notice: Subject to any disclaimer, the term of this patent is extended or adjusted under 35 U.S.C. 154(b) by 355 days.

(21) Appl. No.: 11/232,341

(22) Filed: Sep. 20, 2005

Related U.S. Application Data

(60) Provisional application No. 60/612,923, filed on Sep. 24, 2004.

(51) Int. Cl.
*A61K 31/4164* (2006.01)
*C07D 233/30* (2006.01)
(52) U.S. Cl. .................. 514/392; 548/300.1; 548/316.4; 548/325.1; 514/385; 514/386
(58) Field of Classification Search ............. 548/300.1, 548/316.4, 325.1; 514/385, 386, 392
See application file for complete search history.

(56) References Cited

U.S. PATENT DOCUMENTS

| | | | |
|---|---|---|---|
| 4,798,843 A | 1/1989 | Kruse | |
| 6,124,300 A | 9/2000 | Rajagopalos | |
| 6,486,187 B1 | 11/2002 | Venet | |
| 7,091,232 B2 * | 8/2006 | Chow et al. ................. | 514/386 |
| 7,141,579 B2 * | 11/2006 | Kawashima et al. ........ | 514/300 |
| 7,141,597 B2 * | 11/2006 | Chow et al. ................. | 514/392 |
| 7,312,238 B2 * | 12/2007 | Chow et al. ................. | 514/392 |
| 7,323,485 B2 * | 1/2008 | Chow et al. ................. | 514/396 |

FOREIGN PATENT DOCUMENTS

| | | |
|---|---|---|
| GB | 1499485 | 2/1979 |
| JP | 06067368 | 3/1994 |
| JP | 2002097310 | 4/2002 |
| JP | 2002097312 | 4/2002 |
| WO | WO 99/28200 | 6/1999 |
| WO | WO 01/00586 | 1/2001 |
| WO | WO 02/36162 | 5/2002 |
| WO | WO 03/099795 | 12/2003 |

OTHER PUBLICATIONS

Kruse et al (1989): STN International HCAPLUS database, Columbus (OH), accession No. 1989: 439367.*
Loksha et al (2002): STN International HCAPLUS database, Columbus (OH), accession No. 2002: 389433.*
Ruffolo, Jr., "α-*Adrenoreceptors*": *Molecular Biology, Biochemistry and Pharmacology*, (*Progress in Basic and Clinical Pharmacology series, Karger, 1991*).
Messier et al, High Throughput Assays of Cloned Adrenergic, Muscarinic, Neurokinin, and Neurotrophin Receptors in Living Mammalian Cells, 1995, 76, pp. 308-311.
Conklin et al, "Substitution of three amino acids switches receptor specificity of Gqα to that of G1α", 1993, Nature 363: 274-6.
Dirig et al, "Characterization of variables defining hindpaw withdrawal latency evoked by radiant thermal stimuli",J. Neurosci. Methods, 1997, 76: 183-191.
Hargreaves et al, "A new and sensitive method for measuring thermal nociception in cutaneous hyperalgesia", 1988, Pain 32: 77-88.
Dixon, W.J., "Efficient Analysis of Experimental Observations", Ann. Rev. Pharmacol. Toxicol., 1980, 20: 441-462.
Minami et al, "Allodynia evoked by intrathecal administration of prostaglandin $E_2$ to conscious mice", 1994, 57 Pain, 217-223.

\* cited by examiner

*Primary Examiner*—Golam M Shameem
(74) *Attorney, Agent, or Firm*—John E. Wurst; Kevin J. Forrestal; Allergan, Inc.

(57) ABSTRACT

Compounds of Formula 1

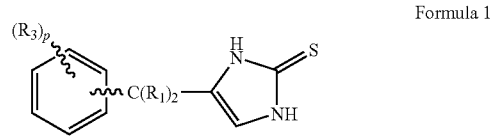

Formula 1 where the variables have the meaning defined in the specification are agonists of $alpha_2$ adrenergic receptors. Several compounds of the disclosure are specific or selective to $alpha_{2B}$ and/or $alpha_{2C}$ adrenergic receptors in preference over $alpha_{2A}$ adrenergic receptors. Additionally some of the claimed compounds have no or only minimal cardiovascular and/or sedatory activity. The compounds of Formula 1 are useful as medicaments in mammals, including humans, for treatment of diseases and or alleviations of conditions which are responsive to treatment by agonists of $alpha_2$ adrenergic receptors. Compounds of Formula 1 which have no significant cardiovascular and/or sedatory activity are useful for treating pain and other conditions with minimal side effects.

2 Claims, No Drawings

4-(PHENYLMETHYL AND SUBSTITUTED PHENYLMETHYL)-IMIDAZOLE-2-THIONES ACTING AS SPECIFIC ALPHA2 ADRENERGIC AGONISTS

This application claims priority to Provisional Patent Application 60/612,923, filed 24 Sep. 2004, which is incorporated by reference herein.

BACKGROUND OF THE INVENTION

1. Field of the Invention

The present invention relates to 4-(phenylmethyl and 4-substituted phenylmethyl)-imidazole-2-thiones and to their use as agonists, preferably specific or selective agonists of $alpha_2$ adrenergic receptors. More specifically the present invention relates to the above-noted compounds, to pharmaceutical compositions containing these compounds as active ingredient for modulating the alpha2 adrenergic receptors, and even more specifically for utilizing these compounds and pharmaceutical compositions to alleviate chronic pain, allodynia, muscle spasticity, diarrhea, neuropathic pain and other diseases and conditions.

2. Background Art

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors tend to bind norepinephrine more strongly than epinephrine and much more strongly than the synthetic compound isoproterenol. The preferred binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$, and $\beta_2$ subtypes. Functional differences between $\alpha_1$ and $\alpha_2$ receptors have been recognized, and compounds which exhibit selective binding between these two subtypes have been developed. Thus, in published international patent application WO 92/0073, the selective ability of the R(+) enantiomer of terazosin to selectively bind to adrenergic receptors of the $\alpha_1$ subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, was said to be limited by their $\alpha_2$ adrenergic receptor mediated induction of increased plasma catecholamine concentration and the attendant physiological sequelae (increased heart rate and smooth muscle contraction).

For a further general background on the α-adrenergic receptors, the reader's attention is directed to Robert R. Ruffolo, Jr., α-Adrenoreceptors: Molecular Biology, Biochemistry and Pharmacology, (Progress in Basic and Clinical Pharmacology series, Karger, 1991), wherein the basis of $\alpha_1/\alpha_2$ subclassification, the molecular biology, signal transduction, agonist structure-activity relationships, receptor functions, and therapeutic applications for compounds exhibiting α-adrenergic receptor affinity is explored.

The cloning, sequencing and expression of alpha receptor subtypes from animal tissues has led to the subclassification of the ($\alpha_1$ adrenoreceptors into $\alpha_{1A}$, $\alpha_{1B}$, and $\alpha_{1D}$. Similarly, the $\alpha_2$ adrenoreceptors have also been classified $\alpha_{2A}$, $\alpha_{2B}$, and $\alpha_{2C}$ receptors. Each $\alpha_2$ receptor subtype appears to exhibit its own pharmacological and tissue specificities. Compounds having a degree of specificity for one or more of these subtypes may be more specific therapeutic agents for a given indication than an $\alpha_2$ receptor pan-agonist (such as the drug clonidine) or a pan-antagonist.

Among other indications, such as the treatment of glaucoma, hypertension, sexual dysfunction, and depression, certain compounds having alpha$_2$ adrenergic receptor agonist activity are known analgesics. However, many compounds having such activity do not provide the activity and specificity desirable when treating disorders modulated by alpha$_2$ adrenoreceptors. For example, many compounds found to be effective agents in the treatment of pain are frequently found to have undesirable side effects, such as causing hypotension and sedation at systemically effective doses. There is a need for new drugs that provide relief from pain without causing these undesirable side effects. Additionally, there is a need for agents which display activity against pain, particularly chronic pain, such as chronic neuropathic and visceral pain.

PCT Publication WO 03/099795 published on Dec. 4, 2003 describes 4-(substituted cycloalkylmethyl) imidazole-2-thiones, 4-(substituted cycloalkenylmethyl) imidazole-2-thiones and related compounds and their use as specific or selective agonists of alpha$_{2B}$ and/or alpha$_{2C}$ adrenergic receptors.

PCT Publication WO 02/36162 published on May 10, 2002 discloses some cylcoalkenyl-methyl-imidazoles, condensed cyclic-methyl imidazoles and an imidazole thione of the following structure

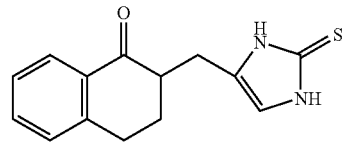

as an alpha$_{2B}$ or alpha$_{2C}$ selective agonist utilized for treatment of ocular neovascularization.

British Patent 1 499 485, published Feb. 1, 1978 describes certain thiocarbamide derivatives; some of these are said to be useful in the treatment of conditions such as hypertension, depression or pain.

PCT Publications WO01/00586 published on Jan. 4, 2001 and WO99/28300 published on Jun. 10, 1999 describe certain imidazole derivatives acting as agonists of alpha$_{2B}$ and/or alpha$_{2C}$ adrenergic receptors. U.S. Pat. No. 6,313,172 discloses phenylmethyl-thiourea derivatives used for treatment of pain.

U.S. Pat. No. 4,798,843 describes (phenyl)-imidazole-2-thiones and substituted (phenyl)-imidazole-2-thiones.

U.S. Pat. Nos. 6,124,330 and 6,486,187 describe imidazole derivatives having activity against disorders of keratinization, such as psoriasis.

Japanese Patent No. 06067368 discloses N-phenyl-imidazole-thiones. Japanese Patent Nos. 2002097310 and 2002097312 disclose additional imidazole derivatives.

U.S. Pat. Nos. 6,545,182 and 6,313,172 describe phenylmethyl-(2hydroxy)ethylthioureas which have no significant cardiovascular or sedative effects and are useful for alleviating chronic pain and allodynia. U.S. Pat. No. 6,534,542 describes cycloalkyl, cycloalkenyl, cycloalkylmethyl and cycloalkenylmethyl (2-hydroxy)ethylthioureas and their use as specific or selective agonists of $alpha_{2B}$ adrenergic receptors.

SUMMARY OF THE INVENTION

The present invention is directed to compounds of Formula 1

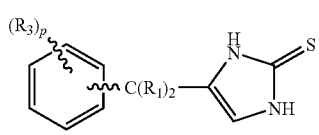

Formula 1 where $R_1$ is independently H, alkyl of 1 to 4 carbons, fluoro substituted alkyl of 1 to 4 carbons, $(CH_2)_n CN$, $(CH_2)_n—OR_2$, $(CH_2)_n—NR_4R_5$;

n is an integer selected from 1, 2 and 3;

$R_2$ is independently H, alkyl of 1 to 4 carbons, $C(O)R_4$, carbocyclic aryl or heterocyclic aryl having 1 to 3 heteroatoms independently selected from N, O and S;

p is an integer selected from 0, 1, 2, 3, 4 and 5;

$R_3$ is independently selected from the groups consisting of alkyl of 1 to 4 carbons, fluoro substituted alkyl of 1 to 4 carbons, alkenyl of 2 to 4 carbons, alkynyl of 2 to 4 carbons, F, Cl, Br, I, $N_3$, $NO_2$, $(CH_2)_q—OR_2$, $(CH_2)_q—NR_5R_6$, $(CH_2)_q—CN$, $C(O)R_4$, $C(O)OR_4$, $(CH_2)_q—SO_2R_4$, carbocyclic aryl or heterocyclic aryl having 1 to 3 heteroatoms independently selected from N, O and S;

q is an integer selected from 0, 1, 2 and 3;

$R_4$ is H, alkyl of 1 to 4 carbons, carbocyclic aryl or heterocyclic aryl having 1 to 3 heteroatoms independently selected from N, O and S;

$R_5$ and $R_6$ independently are H, alkyl of 1 to 4 carbons, $C(O)R_4$ or benzyl, with the proviso that the claim does not include the compound of the formula

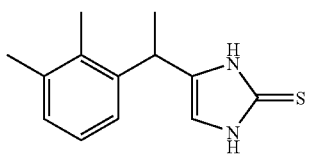

In a second aspect the present invention is directed to pharmaceutical compositions containing as the active ingredient one or more compounds of Formula 1, the compositions being utilized as medicaments in mammals, including humans, for treatment of diseases and or alleviations of conditions which are responsive to treatment by agonists of alpha$_2$ adrenergic receptors. The compositions containing the compounds of the invention are primarily, but not exclusively, used for alleviation of chronic pain and/or allodynia. Some of the compounds of the invention have the demonstrable advantageous property that they are specific or selective to $alpha_{2B}$ and/or $alpha_{2C}$ adrenergic receptors in preference over $alpha_{2A}$ adrenergic receptors. In addition, some of the alpha 2 agonist compounds have no or only minimal cardiovascular and/or sedatory activity.

DETAILED DESCRIPTION OF THE INVENTION

A general description of the compounds of the invention is provided in the Summary section of the present application for patent with reference to Formula 1. It will be readily apparent to those skilled in the art that some of the compounds depicted in these formulas may exist in trans (E) and cis (Z) isomeric forms. Moreover, some of the compounds of the invention may contain one or more asymmetric centers, such that the compounds may exist in enantiomeric as well as in diastereomeric forms. Unless it is specifically noted otherwise, the scope of the present invention includes all trans (E) and cis (Z) isomers, enantiomers, diastereomers and racemic mixtures. Some of the compounds of the invention may form salts with pharmaceutically acceptable acid or base, and such pharmaceutically acceptable salts of the compounds of Formula 1 are also within the scope of the invention.

The imidazole-2-thione compounds of the present invention can undergo tautomeric transformations and can be depicted by the tautomeric formulas shown below. All tautomers of Formula 1 are within the scope of the invention.

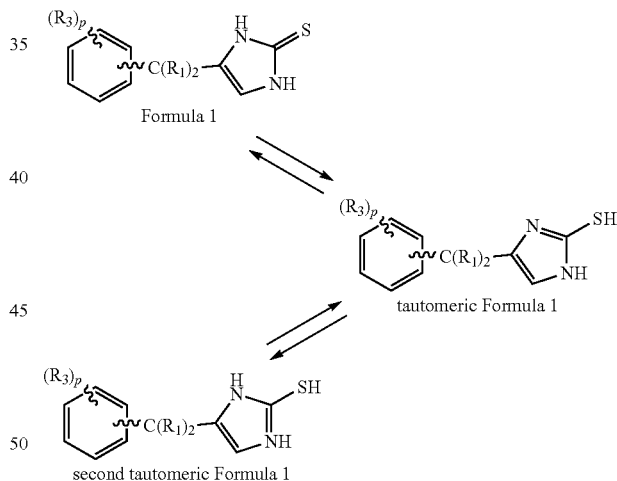

Generally speaking and referring to Formula 1, in the preferred compounds of the invention the variable $R_1$ is H, alkyl of 1 to 4 carbons, or $CH_2OR_2$. Even more preferably one of the $R_1$ groups is H and the other is alkyl of 1 to 4 carbons. Still more preferably one of the $R_1$ groups is methyl and the other is H.

The variable p in the presently preferred compounds of the invention is 2 or zero (0), the latter meaning that there is no $R_3$ substituent on the aromatic portion of the compounds of the invention. In the preferred compounds of the invention where p is 2 the substituents preferably are independently selected from the halogens F, Cl, Br and I and from fluoro substituted alkyl groups having 1 to 4 carbons. Even more preferably when p is 2 the substituents are independently selected from F, Cl and CF$_3$. Alternatively R$_3$ preferably is a CH$_2$OH group in meta position relative to the C(R$_1$)$_2$ group.

In the preferred compounds of the invention the two R$_3$ substituents are in ortho and in meta positions on the phenyl ring relative to the C(R$_1$)$_2$ moiety.

The presently most preferred compounds of the invention are disclosed by their structural formulas in Table 1 together with their activity in assays measuring their ability to act as agonists of alpha$_{2A}$, alpha$_{2B}$ and alpha$_{2C}$ adrenergic receptors.

TABLE 1

Biological Data: Intrinsic Activity

| Structure | Alpha 2A | Alpha 2B | Alpha 2C |
|---|---|---|---|
| Compound 1 | 0.87 | 0.85 | 1.03 |
| Compound 2 | 0.66 | 0.99 | 0.83 |
| Compound 3 | 0.88 | 1.04 | 0.84 |
| Compound 4 | NA | 1.11 | NA |

General Methods for Obtaining the Compounds of the Invention

Reaction Schemes A and B illustrate general methods for obtaining the 4-(substituted-phenyl-methyl)-imidazole-2-thiones).

Reaction Scheme A employs a ketone of Formula 2 which can be obtained through commercial sources or prepared in accordance with known procedures in the chemical scientific and patent literature or by modifications of known procedures which are readily apparent to the practicing synthetic organic chemist. The variable R$_1$ is defined as in connection with Formula 1. The compound of Formula 2 is reacted with a Grignard reagent of 4-iodo-1-triphenylmethyl (trityl)-1H-imidazole (see Cliff et. al. Synthesis (1994) 681 incorporated herein by reference) to provide the trityl protected hydroxy-imidazole compounds of Formula 3. Deoxygenation of the bridging hydroxyl moiety is accomplished by several methods known in the art, such as treatment with trifluoroacetic acid in triethyl silane, followed by acidic deprotection of the trityl group to give a mixture of compounds of Formula 4 and vinylogous material (via an elimination pathway). Reduction of the vinylogous material also produces imidazoles of Formula 4. The imidazoles of Formula 4 are reacted with phenyl chlorothionoformate in the presence of sodium bicarbonate and water and subsequently treated with a base, such as triethylamine to produce 4-(substituted-pheny-methyl)-imidazole-2-thiones of Formula 1.

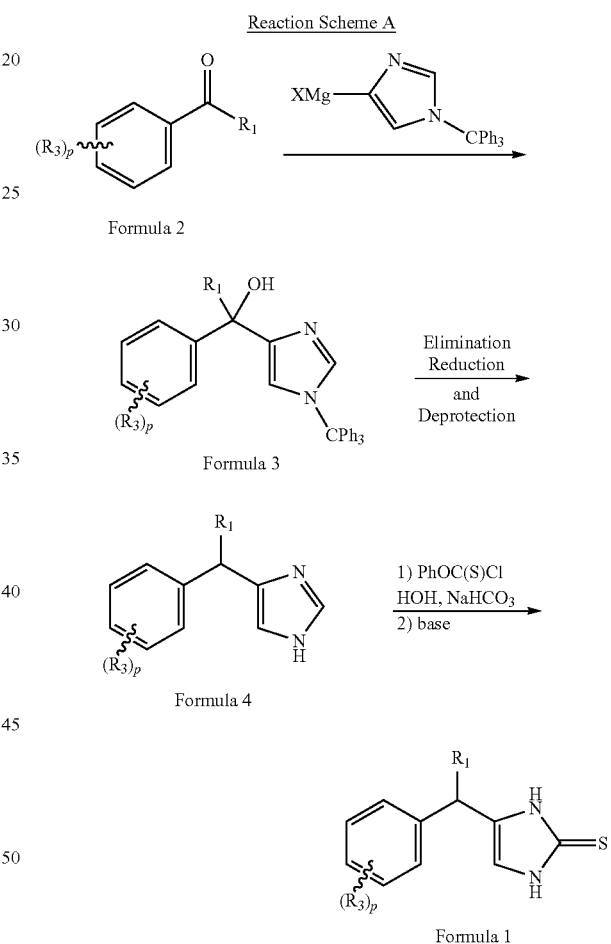

Reaction Scheme A

Reaction Scheme B employs an aldehyde starting material of Formula 5 which can be obtained through commercial sources or prepared in accordance with known procedures in the chemical scientific and patent literature or by modifications of known procedures which are readily apparent to the practicing synthetic organic chemist. The aldehyde of Formula 5 is reacted with tosyl methylisocyanide (TosMIC) and sodium cyanide and thereafter heated in the presence of excess ammonia to produce the imidazole compounds of Formula 6. The imidazoles of Formula 6 are reacted with pheny chlorothionoformate as described above to obtain compounds of Formula 1.

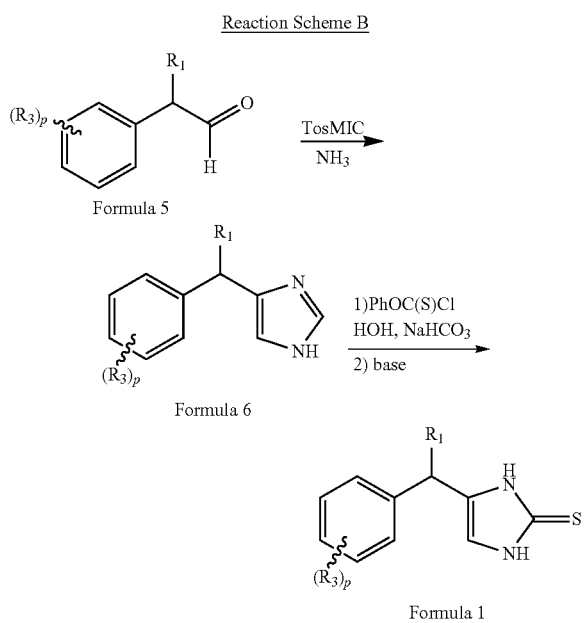

Reaction Scheme B

Biological Activity, Modes of Administration

The imidazole-2-thione compounds of the invention are agonists of alpha$_2$ adrenergic receptors. The alpha$_2$ receptor activity of the compounds of the invention is demonstrated in an assay titled Receptor Selection and Amplification technology (RSAT) assay, which is described in the publication by Messier et. Al., 1995, Pharmacol. Toxicol. 76, pp. 308-311 (incorporated herein by reference) and is also described below. Another reference pertinent to this assay is Conklin et al. (1993) Nature 363:274-6, also incorporated herein by reference.

Receptor Selection and Amplification Technology (RSAT) Assay

The RSAT assay measures a receptor-mediated loss of contact inhibition that results in selective proliferation of receptor-containing cells in a mixed population of confluent cells. The increase in cell number is assessed with an appropriate transfected marker gene such as β-galactosidase, the activity of which can be easily measured in a 96-well format. Receptors that activate the G protein, Gq, elicit this response. Alpha2 receptors, which normally couple to Gi, activate the RSAT response when coexpressed with a hybrid Gq protein that has a Gi receptor recognition domain, called Gq/i5.

NIH-3T3 cells are plated at a density of 2×10$^6$ cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 μl added to 100 μl aliquots of various concentrations of drugs in triplicate in 96-well dishes. Incubations continue 72-96 hr at 37° C. After washing with phosphate-buffered saline, β-galactosidase enzyme activity is determined by adding 200 μl of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the alpha$_{2A}$, alpha$_{2B}$ and alpha$_{2C}$ receptors.

brimonidine

Diseases that may be treated with this invention include, but are not limited to neurodegenerative aspects of the following conditions:

MACULOPATHIES/RETINAL DEGENERATION Non-Exudative Age Related Macular Degeneration (ARMD), Exudative Age Related Macular Degeneration (ARMD), Choroidal Neovascularization, Diabetic Retinopathy, Central Serous Chorioretinopathy, Cystoid Macular Edema, Diabetic Macular Edema, Myopic Retinal Degeneration, UVEITIS/RETINITIS/CHOROIDITIS/OTHER INFLAMMATORY DISEASES Acute Multi focal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome, Punctate Inner Choroidopathy, Acute Posterior Multifocal Placoid Pigment Epitheliopathy, Acute Retinal Pigement Epitheliitis, Acute Macular Neuroretinopathy VASCULAR DISEASES/EXUDATIVE DISEASES Diabetic retinopathy, Retinal Arterial Occlusive Disease, Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angiitis, Sickle Cell Retinopathy and other Hemoglobinopathies, Angioid Streaks, Familial Exudative Vitreoretinopathy, Eales Disease TRAUMATIC/SURGICAL/ENVIRONMENTAL Sympathetic Ophthalmia, Uveitic Retinal Disease, Retinal Detachment, Trauma, Laser, PDT, Photocoagulation, Hypoperfusion During Surgery, Radiation Retinopathy, Bone Marrow Transplant Retinopathy PROLIFERATIVE DISORDERS Proliferative Vitreal Retinopathy and Epiretinal Membranes INFECTIOUS DISORDERS Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associate with HIV Infection, Uveitic Disease Associate with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis GENETIC DISORDERS Retinitis Pigmentosa, Systemic Disorders with Accosiated Retinal Dystrophies, Congenital Stationary Night Blindness, Cone Dystrophies, Stargardt's Disease And Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum RETINAL TEARS/HOLES Retinal Detachment, Macular Hole, Giant Retinal Tear TUMORS Retinal Disease Associated With Tumors, Congenital Hypertrophy Of The RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, Intraocular Lymphoid Tumors.

The results of the RSAT assay with several exemplary compounds of the invention are disclosed in Table 1 above together with the chemical formulas of these examplary compounds. NA stands for "not active" at concentrations less than 10 micromolar.

Generally speaking $alpha_2$ agonists, can alleviate sympathetically-sensitized conditions that are typically associated with periods of stress. These include the neurological conditions of 1) increased sensitivity to stimuli such as intracranial pressure, light and noise characteristic of migraines and other headaches; 2) the increased sensitivity to colonic stimuli characteristic of Irritable Bowel Syndrome and other GI disorders such as functional dyspepsia; 3) the sensation of itch associated with psoriasis and other dermatological conditions; 4) muscle tightness and spasticity; 5) sensitivity to normally innocuous stimuli such as light touch and spontaneous pain characteristic of conditions like fibromyalgia; 6) various cardiovascular disorders involving hypertension, tachycardia, cardiac ischemia and peripheral vasoconstriction; 7) metabolic disorders including obesity and insulin resistance; 8) behavioral disorders such as drug and alcohol dependence, obsessive-compulsive disorder, Tourette's syndrome, attention deficit disorder, anxiety and depression; 9) altered function of the immune system such as autoimmune diseases including lupus erythematosis and dry eye disorders; 10) chronic inflammatory disorders such as Crohn's disease and gastritis; 11) sweating (hyperhydrosis) and shivering; and 12) sexual dysfunction.

Alpha$_2$ agonists including $alpha_{2B/2C}$ agonists are also useful in the treatment of glaucoma, elevated intraocular pressure, neurodegenerative diseases including Alzheimer's, Parkinsons, ALS, schizophrenia, ischemic nerve injury such as stroke or spinal injury, and retinal injury as occurs in glaucoma, macular degeneration, diabetic retinopathy, retinal dystrophies, Lebers optic neuropathy, other optic neuropathies, optic neuritis often associated with multiple sclerosis, retinal vein occlusions, and following procedures such as photodynamic therapy and LASIX. Also included are chronic pain conditions such as cancer pain, post-operative pain, allodynic pain, neuropathic pain, CRPS or causalgia, visceral pain.

A compound is considered selective agonist of $alpha_{2B}$ and/or $alpha_{2C}$ adrenergic receptors in preference over $alpha_{2A}$ receptors, if the compound is more active, preferably at least ten (10) times more active towards either $alpha_{2B}$ or towards $alpha_{2C}$ receptors than towards $alpha_{2A}$ receptors. It is expected that some of the compounds of the invention are agonists of all three alpha$_2$ receptors (pan agonists) and that other compounds of the invention are selective or specific to $alpha_{2B}$ receptors.

Thus, the imidazole-2-thione compounds of the invention are useful for treating neurological condition of conditions and diseases which are responsive to treatment by $alpha_{2B}$ and/or $alpha_{2C}$ adrenergic receptor agonists. Such conditions and diseases include, but are not limited to, pain including chronic pain (which may be, without limitation visceral, inflammatory, referred or neuropathic in origin) neuropathic pain, corneal pain, glaucoma, reducing elevated intraocular pressure, ischemic neuropathies and other neurodegenerative diseases, diarrhea, and nasal congestion. Chronic pain may arise as a result of, or be attendant to, conditions including without limitation: arthritis, (including rheumatoid arthritis), spondylitis, gouty arthritis, osteoarthritis, juvenile arthritis, and autoimmune diseases including without limitation, lupus erythematosus. Visceral pain may include, without limitation, pain caused by cancer or attendant to the treatment of cancer as, for example, by chemotherapy or radiation therapy. In addition, the compounds of this invention are useful for treating muscle spasticity including hyperactive micturition, diuresis, withdrawal syndromes, neurodegenerative diseases including optic neuropathy, spinal ischemia and stroke, memory and cognition deficits, attention deficit disorder, psychoses including manic disorders, anxiety, depression, hypertension, congestive heart failure, cardiac ischemia and nasal congestion, chronic gastrointestinal inflammations, Crohn's disease, gastritis, irritable bowel syndrome (IBS), functional dyspepsia and ulcerative colitis.

The activity of the compounds of the invention is highly advantageous because the administration of these compounds to mammals does not result in sedation or in significant cardiovascular effects (such as changes in blood pressure or heart rate).

The compounds of the invention act and can be used as a highly effective analgesic, particularly in chronic pain models, with minimal undesirable side effects, such as sedation and cardiovascular depression, commonly seen with other agonists of the alpha$_2$ receptors.

The compounds of the invention may be administered at pharmaceutically effective dosages. Such dosages are normally the minimum dose necessary to achieve the desired therapeutic effect; in the treatment of chromic pain, this amount would be roughly that necessary to reduce the discomfort caused by the pain to tolerable levels. Generally, such doses will be in the range 1-1000 mg/day; more preferably in the range 10 to 500 mg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The compounds are useful in the treatment of pain in a mammal; particularly a human being. Preferably, the patient will be given the compound orally in any acceptable form, such as a tablet, liquid, capsule, powder and the like. However, other routes may be desirable or necessary, particularly if the patient suffers from nausea. Such other routes may include, without exception, transdermal, parenteral, subcutaneous, intranasal, intrathecal, intramuscular, intravenous, and intrarectal modes of delivery. Additionally, the formulations may be designed to delay release of the active compound over a given period of time, or to carefully control the amount of drug released at a given time during the course of therapy.

Another aspect of the invention is drawn to therapeutic compositions comprising the compounds of Formula 1 and pharmaceutically acceptable salts of these compounds and a pharmaceutically acceptable excipient. Such an excipient may be a carrier or a diluent; this is usually mixed with the active compound, or permitted to dilute or enclose the active compound. If a diluent, the carrier may be solid, semi-solid, or liquid material that acts as a excipient or vehicle for the active compound. The formulations may also include wetting agents, emulsifying agents, preserving agents, sweetening agents, and/or flavoring agents. If used as in an ophthalmic or infusion format, the formulation will usually contain one or more salt to influence the osmotic pressure of the formulation.

In another aspect, the invention is directed to methods for the treatment of pain, particularly chronic pain, through the administration of one or more compounds of Formula 1 or pharmaceutically acceptable salts thereof to a mammal in need thereof. As indicated above, the compound will usually be formulated in a form consistent with the desired mode of delivery.

It is known that chronic pain (such as pain from cancer, arthritis, and many neuropathic injuries) and acute pain (such as that pain produced by an immediate mechanical stimulus, such as tissue section, pinch, prick, or crush) or by modifications of known procedures which are readily apparent to the practicing synthetic organic chemist. The amine of Formula 10 is reacted with a base such as potassium hydroxide or sodium carbonate and 4-chloromethyl-1-trityl-imidazole or 4-hydroxymethyl-imidazole and thereafter deprotected to produce the imidazole compounds of Formula 11. The imidazoles of Formula 11 were reacted with phenychlorothionoformate as described above to obtain compounds of Formula 12.

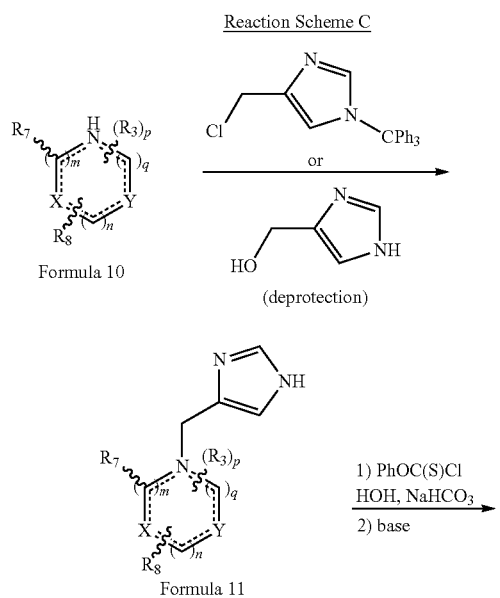

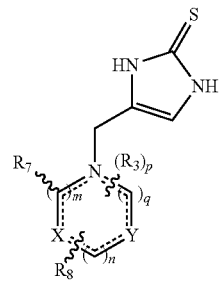

Formula 12

Biological Activity, Modes of Administration

The imidazole-2-thione compounds of the invention are agonists of alpha$_2$ adrenergic receptors. The alpha$_2$ receptor activity of the compounds of the invention is demonstrated in an assay titled Receptor Selection and Amplification technology (RSAT) assay, which is described in the publication by Messier et. Al., 1995, Pharmacol. Toxicol. 76, pp. 308-311 (incorporated herein by reference) and is also described below. Another reference pertinent to this assay is Conklin et al. (1993) Nature 363:274-6, Receptor Selection and Amplification Technology (RSAT) assay, also incorporated herein by reference.

The RSAT assay measures a receptor-mediated loss of contact inhibition that results in selective proliferation of receptor-containing cells in a mixed population of confluent cells. The increase in cell number is assessed with an appropriate transfected marker gene such as $\beta$-galactosidase, the activity of which can be easily measured in a 96-well format. Receptors that activate the G protein, Gq, elicit this response. Alpha2 receptors, which normally couple to Gi, activate the RSAT response when coexpressed with a hybrid Gq protein that has a Gi receptor recognition domain, called Gq/i5.

NIH-3T3 cells are plated at a density of 2×10$^6$ cells in 15 cm dishes and maintained in Dulbecco's modified Eagle's medium supplemented with 10% calf serum. One day later, cells are cotransfected by calcium phosphate precipitation with mammalian expression plasmids encoding p-SV-β-galactosidase (5-10 μg), receptor (1-2 μg) and G protein (1-2 μg). 40 μg salmon sperm DNA may also be included in the transfection mixture. Fresh media is added on the following day and 1-2 days later, cells are harvested and frozen in 50 assay aliquots. Cells are thawed and 100 μl added to 100 μl aliquots of various concentrations of drugs in triplicate in 96-well dishes. Incubations continue 72-96 hr at 37° C. After washing with phosphate-buffered saline, $\beta$-galactosidase enzyme activity is determined by adding 200 μl of the chromogenic substrate (consisting of 3.5 mM o-nitrophenyl-β-D-galactopyranoside and 0.5% nonidet P-40 in phosphate buffered saline), incubating overnight at 30° C. and measuring optical density at 420 nm. The absorbance is a measure of enzyme activity, which depends on cell number and reflects a receptor-mediated cell proliferation. The efficacy or intrinsic activity is calculated as a ratio of the maximal effect of the drug to the maximal effect of a standard full agonist for each receptor subtype. Brimonidine, also called UK14304, the chemical structure of which is shown below, is used as the standard agonist for the alpha$_{2A}$, alpha$_{2B}$ and alpha$_{2C}$ receptors.

Another embodiment is a method where the mammal is administered the composition for treating glaucoma.

Another embodiment is a method where the mammal is administered the composition for treating neuropathies or neurodegenerative diseases.

Another embodiment is a method where the mammal is administered the composition for treating muscle spasticity.

The following in vivo assays can be employed to demonstrate the biological activity of the compounds of the invention.

Sedative Activity

To test sedation, six male Sprague-Dawley rats are given up to 3 mg/kg of the test compound in a saline or DMSO vehicle by intraperitoneal injection (i.p.). Sedation is graded 30 minutes following administration of the drug by monitoring locomotor skills as follows.

The Sprague-Dawley rats are weighed and 1 ml/kg body weight of an appropriate concentration (ie. 3 mg/ml for a final dose of 3 mg/kg) drug solution is injected intraperitoneally. Typically the test compound is formulated in approximately 10 to 50% DMSO. The results are compared to controls that are injected with 1 ml/kg saline or 10 to 50% DMSO. Rat activity is then determined 30 minutes after injection of the drug solution. Rats are placed in a dark covered chamber and a digicom analyzer (Omnitech Electronic) quantitates their exploratory behavior for a five-minute period. The machine records each time the rat interrupts an array of 32 photoelectric beams in the X and Y orientation.

Representative Compounds 1 and 3 of the invention were tested in this assay intraperitoneally and up to a dose of 1 mg/kg, and were found to have no sedative effect. The results in this test with other compounds of the invention are also expected to show that the compounds of the invention have no significant sedatory activity.

Effects on Cardiovascular System

To test the effect of the compounds on the cardiovascular system, typically six cynomolgus monkeys are given 500 µg/kg of the test compound by intravenous injection (i.v.) Or 3 mg/kg by oral gavage. The effects of the compound on the animals' blood pressure and heart rate is measured at time intervals from 30 minutes to six hours following administration of the drug. The peak change from a baseline measurement taken 30 minutes before drug administration is recorded using a blood pressure cuff modified for use on monkeys.

Specifically and typically the monkeys are weighed (approximately 4 kg) and an appropriate volume (0.1 ml/kg) of a 5 mg/ml solution of the test compound formulated in 10 to 50% DMSO is injected into the cephalic vein in the animals' arm. Cardiovascular measurements are made with a BP 100S automated sphygmomanometer (Nippon Colin, Japan) at 0.5, 1, 2, 4 and 6 hours.

The results of this test are expected to show that the compounds of the invention have no or only minimal detectable effect on the cardiovascular system.

Alleviation of Acute Pain

Models to measure sensitivity to acute pain have typically involved the acute application of thermal stimuli; such a stimulus causes a programmed escape mechanism to remove the affected area from the stimulus. The proper stimulus is thought to involve the activation of high threshold thermoreceptors and C fiber dorsal root ganglion neurons that transmit the pain signal to the spinal cord.

The escape response may be "wired" to occur solely through spinal neurons, which receive the afferent input from the stimulated nerve receptors and cause the "escape" neuromuscular response, or may be processed supraspinally—that is, at the level of the brain. A commonly used method to measure nociceptive reflexes involves quantification of the withdrawal or licking of the rodent paw following thermal excitation. See Dirig, D. M. et al., *J. Neurosci. Methods* 76:183-191 (1997) and Hargreaves, K. et al., *Pain* 32:77-88 (1988), hereby incorporated by reference herein.

In a variation of this latter model, male Sprague-Dawley rats are tested by being placed on a commercially available thermal stimulus device constructed as described in Hargreaves et al. This device consists of a box containing a glass plate. The nociceptive stimulus is provided by a focused projection bulb that is movable, permitting the stimulus to be applied to the heel of one or both hindpaws of the test animal. A timer is actuated with the light source, and the response latency (defined as the time period between application of the stimulus and an abrupt withdrawal of the hindpaw) is registered by use of a photodiode motion sensor array that turns off the timer and light. Stimulus strength can be controlled by current regulation to the light source. Heating is automatically terminated after 20 seconds to prevent tissue damage.

Typically four test animals per group are weighed (approximately 0.3 kg) and injected intraperitonealy (i.p.) with 1 ml/kg of the test compound formulated in approximately 10 to 50% dimethylsulfoxide (DMSO) vehicle. Animals typically receive a 0.1 mg/kg and a 1 mg/kg dose of the three compounds. Rats are acclimated to the test chamber for about 15 minutes prior to testing. The paw withdrawal latency is measured at 30, 60 and 120 minutes after drug administration. The right and left paws are tested 1 minute apart, and the response latencies for each paw are averaged. Stimulus intensity is sufficient to provide a temperature of 45-50 degrees centigrade to each rat hindpaw.

Alleviation of Chronic Pain

A model in accordance with *Kim and Chung* 1992, Pain 150, pp 355-363 (Chung model), for chronic pain (in particular peripheral neuropathy) involves the surgical ligation of the L5 (and optionally the L6) spinal nerves on one side in experimental animals. Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to pain from low-threshold mechanical stimuli, such as that producing a faint sensation of touch in a human, within about 1 week following surgery. This sensitivity to normally non-painful touch is called "tactile allodynia" and lasts for at least two months. The response includes lifting the affected hindpaw to escape from the stimulus, licking the paw and holding it in the air for many seconds. None of these responses is normally seen in the control group.

Rats are anesthetized before surgery. The surgical site is shaved and prepared either with betadine or Novacaine. Incision is made from the thoracic vertebra XIII down toward the sacrum. Muscle tissue is separated from the spinal vertebra (left side) at the L4-S2 levels. The L6 vertebra is located and the transverse process is carefully removed with a small rongeur to expose the L4-L6 spinal nerves. The L5 and L6 spinal nerves are isolated and tightly ligated with 6-0 silk thread. The same procedure is done on the right side as a control, except no ligation of the spinal nerves is performed.

A complete hemostasis is confirmed, then the wounds are sutured. A small amount of antibiotic ointment is applied to the incised area, and the rat is transferred to the recovery plastic cage under a regulated heat-temperature lamp. On the day of the experiment, at least seven days after the surgery, typically six rats per test group are administered the test drugs by intraperitoneal (i.p.) injection or oral gavage. For i.p. injection, the compounds are formulated in d H₂O and given in a volume of 1 ml/kg body weight using an 18-gauge, 3 inch gavage needle that is slowly inserted through the esophagus into the stomach.

Tactile allodynia is measured prior to and 30 minutes after drug administration using von Frey hairs that are a series of fine hairs with incremental differences in stiffness. Rats are placed in a plastic cage with a wire mesh bottom and allowed to acclimate for approximately 30 minutes. The von Frey hairs are applied perpendicularly through the mesh to the mid-plantar region of the rats' hindpaw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair. The 50% paw withdrawal threshold is determined using the method of Dixon, W. J., *Ann. Rev. Pharmacol. Toxicol.* 20:441-462 (1980) hereby incorporated by reference. The post-drug threshold is compared to the pre-drug threshold and the percent reversal of tactile sensitivity is calculated based on a normal threshold of 15.1 grams.

The Mouse Sulprostone Model is an alternative model in which chronic pain, allodynia can be induced in mice through intrathecal treatment of the animals with 200 ng sulprostone (prostaglandin E2 receptor agonist) in 50% DMSO and in volume of 5 µl. In this model, the pain response to stroking the flank with a paint brush is scored 8 times over a 35 minute period starting 15 minutes following final administration of sulprostone. Minami et al., 57 Pain 217-223 (1994), hereby incorporated by reference. Sulprostone treatment alone elicits a score of 12-13 on a 16-point scale.

In variants of this model, allodynia can be induced using intraperitoneal injection of 300 µg/kg sulprostone or 30 µg/kg phenylephrine. Alternatively allodynia can be induced using intrathecal injection of 100 ng N-methyl-D-asparate (NMDA) or 30 ng phenylephrine (PE) formulated in dH₂O in a volume of e.g. 5 microliters.

In either model, the compounds are formulated in dH₂O and given in a volume of 1 ml/kg body weight for intraperitoneal (IP) dosing.

The compounds of the invention are expected to be useful as analgesics to alleviate pain.

Specific Embodiments, Experimental

Example A

Method A: Procedure for the preparation of 4-[1-(2,3-dichloro-phenyl)-ethyl]-1,3-dihydro-imidazole-2-thione (Compound 1)

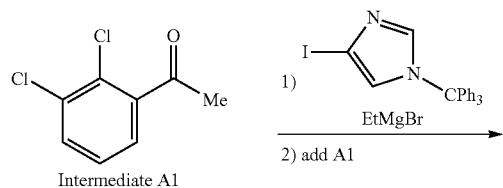

Intermediate A1

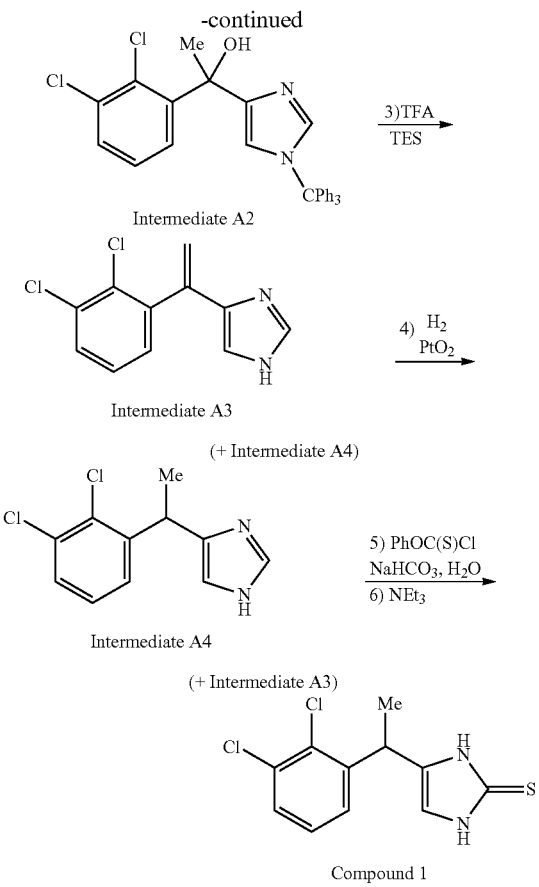

A mixture of 4-iodo-1-tritylimidazole (see Cliff et. al. Synthesis (1994) 681 incorporated herein by reference) (4.4 g, 10.1 mmol) in dichloromethane (44 mL) at room temperature (rt) was treated with ethyl magnesium bromide (3.40 mL, 10.2 mmol, 3M in ether) and allowed to react for 90 minutes. A solution of 2-dichloroacetophenone (commercially available from Lancaster) (Intermediate A1) (1.0 g, 5.02 mmol) in dichloromethane (10 mL) was added via syringe at 20° C. and stirred for 16 h. The mixture was quenched with a saturated solution of ammonium chloride (50 mL) and diluted with dichloromethane: CH₂Cl₂. The organic material was isolated in an aqueous workup followed by extraction with CH₂Cl₂. The residue was purified by chromatography on silica gel with 2% MeOH: CH₂Cl₂ to give 1-(2,3-dichloro-phenyl)-1-(1-trityl-1H-imidazol-4-yl)-ethanol (Intermediate A2) as a solid, 3.8 g.

1-(2,3-dichloro-phenyl)-1-(1-trityl-1H-imidazol-4-yl)-ethanol (Intermediate A2, ~5.02 mmol) in trifluoroacetic acid (TFA) (5 mL) and triethylsilane (TES) (8.0 mL, 50 mmol) was reacted at rt for 18 h. The mixture was evaporated under reduced pressure. The mixture was partitioned between ethyl acetate and 1M NaOH solution. The aqueous layer was extracted with ethyl acetate and the pooled layers were washed with water, brine and dried over MgSO₄. The residue was filtered and the filtrate concentrated onto silica gel. The material was purified by elution from silica gel with 2% NH₃-MeOH: CH₂Cl₂ to yield a 4:1 mixture of 4-[1-(2,3-dichloro-phenyl)-vinyl]-1H-imidazole (Intermediate A3) and 4-[1-(2,3-dichloro-phenyl)-ethyl]-1H-imidazole (Intermediate A4), 0.77 g.

A 4:1 mixture of 4-[1-(2,3-dichloro-phenyl)-vinyl]-1H-imidazole (Intermediate A3) and 4-[1-(2,3-dichloro-phenyl)-ethyl]-1H-imidazole (Intermediate A4), (0.77 g) in methanol and ethyl acetate was reduced by the action of PtO₂ (180 mg) under H₂ at 50 psi for 16 h at rt. The mixture was filtered through Celite and freed of solvent under reduced pressure. The residue was a 1:1 mixture of Intermediate A3 and Intermediate A4 that was used in the next step without further purification.

A 1:1 mixture of 4-[1-(2,3-dichloro-phenyl)-ethyl]-1H-imidazole (Intermediate A4), and 4-[1-(2,3-dichloro-phenyl)-vinyl]-1H-imidazole (Intermediate A3) (0.77 g, 3.2 mmol) in tetrahydrofuran (THF) (10 mL) and water (10 mL) was treated with NaHCO₃ (1.64 g, 19.5 mmol) at rt for 10 m. Phenyl chlorothionoformate (1.1 mL, 7.95 mmol) was added and stirring was continued for 5 h. The mixture was diluted with water and extracted with hexane:ethyl acetate (3×). The organic portions were combined, dried over MgSO₄, filtered and the solvent was removed under vacuum. The residue was dissolved in MeOH (20 mL) and treated with triethylamine (NEt₃) (1 mL) for 18 h at rt. The mixture was concentrated onto silica gel. The material was purified by elution from silica gel with 1 to 2% MeOH: CH₂Cl₂. The solids were titurated with CHCl₃: hexanes and collected on a glass frit to give a white solid 4-[1-(2,3-dichloro-phenyl)-ethyl]-1,3-dihydro-imidazole-2-thione (Compound 1) 40 mg.

$^1$H NMR (300 MHz, DMSO-d$^6$): δ 11.9 (br s, 1H), 11.8 (br s, 1H), 7.52 (dd, J=1.2, 7.8 Hz, 1H), 7.32 (t, J=7.8 Hz, 1H), 7.15 (dd, J=1.6, 7.8 Hz, 1H), 6.62 (br s, 1H), 4.34 (q, J=6.9 Hz, 1H), 1.43 (d, J=6.9 Hz, 3H).

Example A-2 (Compound 2)

Use of 2-fluoroacetophenone (commercially available from Lancaster) in Method A where 10% Pd/C catalyst was used in place of PtO₂ in step 4, produced 4-[1-(2,3-difluoro-phenyl)-ethyl]-1,3-dihydro-imidazole-2-thione (Compound 2). $^1$H NMR (300 MHz, methanol-d$^4$): δ 7.19-7.06 (m, 2H), 6.98-6.92 (m, 1H), 6.64 (d, J=1.2 Hz, 1H), 4.33 (q, J=7.2 Hz, 1H), 1.55 (d, J=7.5 Hz, 3H).

Example B

Method B: Procedure for the preparation 4-[1-(2-fluoro-3-trifluoromethyl-phenyl)-ethyl]-1,3-dihydro-imidazole-2-thione (Compound 3)

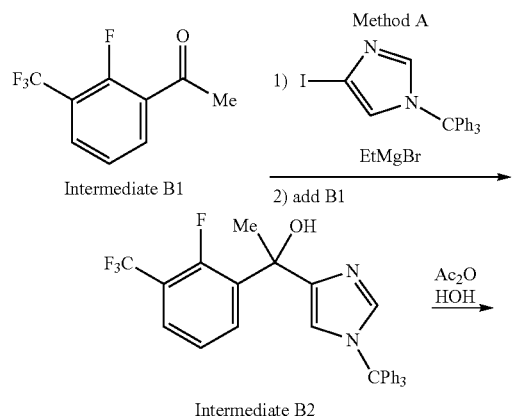

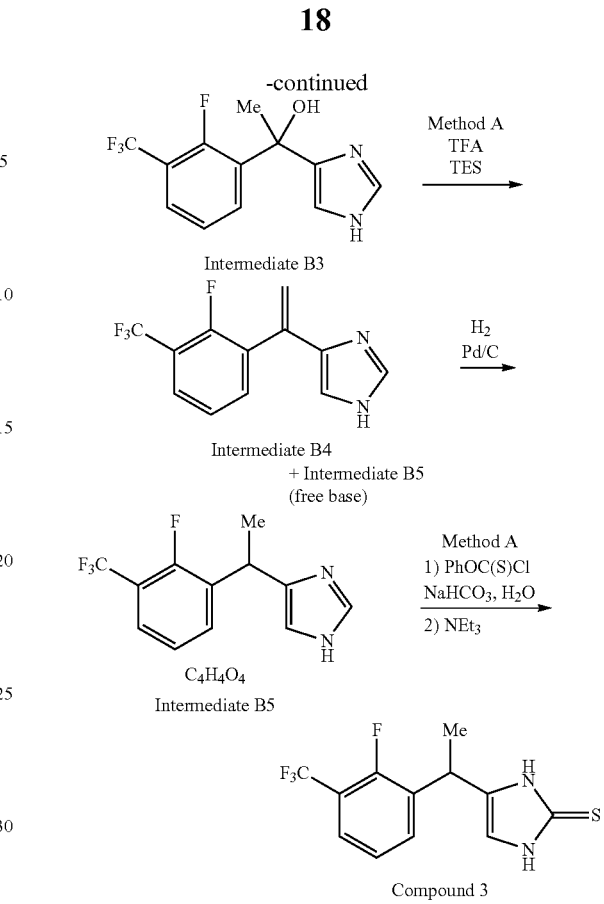

2-Fluoro-3-trifluoromethylacetophenone (Intermediate B1) (commercially available from Lancaster) was subjected to the appropriate process steps (shown in the reaction scheme above) of Method A to give 1-(2-fluoro-3-trifluoromethyl-phenyl)-1-(1-trityl-1H-imidazol-4-yl)-ethanol (Intermediate B2).

1-(2-fluoro-3-trifluoromethyl-phenyl)-1-(1-trityl-1H-imidazol-4-yl)-ethanol (Intermediate B2) (4.7 mmol) in acetic acid (13 mL) and water (3 mL) was heated to 100° C. for 1 h. The mixture was cooled to rt and basified with 2M NaOH. The compound was extracted with ethyl acetate and the solution was concentrated onto silica gel. The product was eluted with 3-5% NH₃-MeOH: CH₂Cl₂ to give 1-(2-fluoro-3-trifluoromethyl-phenyl)-1-(1H-imidazol-4-yl)-ethanol (Intermediate B3) 1.1 g (85%).

1-(2-fluoro-3-trifluoromethyl-phenyl)-1-(1H-imidazol-4-yl)-ethanol (Intermediate B3) (1.0 g, 3.65 mmol) was subjected to treatment with TFA and TES at 55° C. for 28 h as in Method A to give a mixture of 4-[1-(2-fluoro-3-trifluoromethyl-phenyl)-vinyl]-1H-imidazole (Intermediate B4) and a minor amount of 4-[1-(2-Fluoro-3-trifluoromethyl-phenyl)-ethyl]-1H-imidazole (Intermediate B5) as the free base.

4-[1-(2-Fluoro-3-trifluoromethyl-phenyl)-vinyl]-1H-imidazole (Intermediate B4) and Intermediate B5 (~0.80 g, 3.1 mmol) in methanol and ethyl acetate was reduced by the action of 10% Pd/C (130 mg) under H₂ at 40 psi for 16 h at rt. The mixture was filtered through Celite and freed of solvent under reduced pressure. The residue was purified by chromatography on silica gel with 5% NH₃—MeOH: CH₂Cl₂. The imidazole, Intermediate B5 (~0.77 g) compound was treated with 0.9 equivalent of fumaric acid (310 mg). This material was titurated with THF/hexanes to give 4-[1-(2-fluoro-3-trifluoromethyl-phenyl)-ethyl]-1H-imidazole fumaric acid salt (Intermediate B5)~1 g.

4-[1-(2-Fluoro-3-trifluoromethyl-phenyl)-ethyl]-1H-imidazole fumaric acid salt (Intermediate B5) (~1 g) was subjected to the appropriate process steps in Method A to give, pure 4-[1-(2-fluoro-3-trifluoromethyl-phenyl)-ethyl]-1,3-dihydro-imidazole-2-thione (Compound 3), 136 mg.

$^1$H NMR (300 MHz, methanol-d$^4$) δ 7.59 (t, J=6.9 Hz, 1H), 7.45 (t, J=6.6 Hz, 1H), 7.30 (t, J=7.8 Hz, 1H), 6.68 (d, J=0.9 Hz, 1H), 4.40 (q, J=7.5 Hz, 1H), 1.56 (d, J=6.9 Hz, 3H).

Example C

Method C: Procedure for the preparation 4-(1-phenyl-ethyl)-1,3-dihydro-imidazole-2-thione (Compound 4)

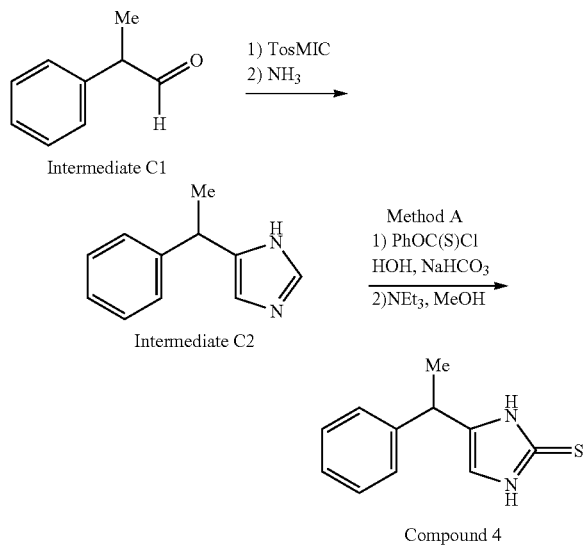

The preparation of Intermediate C2 followed the procedure by Horne, D. A.; Yakushijin, K.; Büchi, G. *Heterocycles*, 1994, 39, 139 incorporated herein by reference. A solution of 2-phenyl-propionaldehyde (Intermediate C1) (0.75 g, 4.57 mmol) in EtOH (15 mL) was treated with tosylmethyl isocyanide (TosMIC) (1.4 g, 7.18 mmol) and NaCN (~10 mg, cat.). The resulting mixture was allowed to stir at rt for 20 minutes. The solvent was removed in vacuo and the residue was dissolved in ~7M NH$_3$ in MeOH (45 mL) and transferred to a resealable tube. This mixture was heated in a re-sealable tube at 90-100° C. for 12 h. Thereafter the mixture was concentrated and purified by chromatography on SiO$_2$ with 5% MeOH (sat. w/NH$_3$):CH$_2$Cl$_2$ to give 5-(1-phenyl-ethyl)-1H-imidazole (Intermediate C2) 0.4 g (31%) as an amber oil.

A solution of 5-(1-phenyl-ethyl)-1H-imidazole (Intermediate C2) (0.20 g, 1.16 mmol) in THF (6 mL) and water (6 mL) was treated with NaHCO$_3$ (0.98 g) at rt for 10 sm. Phenyl chlorothionoformate (0.40 mL, ~3.0 mmol) was added and stirring was continued for 3 h. The mixture was diluted with water (10 mL) and extracted with ether (3×15 mL). The organic portions were combined, dried over MgSO$_4$, filtered and freed of solvent. The residue was dissolved in MeOH (8 mL) and treated with NEt$_3$ (1 mL) for 16 h. The solvent was removed under vacuum and the product was washed on a glass frit with 50% CH$_2$Cl$_2$:hexanes to give 4-(1-phenyl-ethyl)-1,3-dihydro-imidazole-2-thione (Compound 4)

$^1$H NMR (300 MHz, DMSO-d$^6$ w/TMS): δ 11.9 (s, 1H), 11.7 (s, 1H), 7.32-7.21 (m, 5H), 6.55 (s, 1H), 3.89 (q, J=7.2 Hz, 1H), 1.46 (d, J=6.9 Hz, 3H).

What is claimed is:

1. A compound having the formula

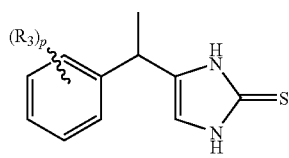

wherein R$_3$ is independently selected from F, Cl and CF$_3$ and p is zero (0) or 2.

2. A compound of the formula

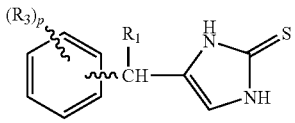

where R$_1$ is alkyl of 1 to 4 carbons, fluoro substituted alkyl of 1 to 4 carbons, (CH$_2$)$_n$CN, (CH$_2$)$_n$—OR$_2$, (CH$_2$)$_n$—NR$_4$R$_5$;

n is an integer selected from 1, 2 and 3;

R$_2$ is independently H, alkyl of 1 to 4 carbons, C(O)R$_4$, carbocyclic aryl or heterocyclic aryl having 1 to 3 heteroatoms independently selected from N, O and S;

p is an integer selected from 0, 1, 2, 3, 4 and 5;

R$_3$ is independently selected from the groups consisting of alkyl of 1 to 4 carbons, fluoro substituted alkyl of 1 to 4 carbons, alkenyl of 2 to 4 carbons, alkynyl of 2 to 4 carbons, F, Cl, Br, I, N$_3$, NO$_2$, (CH$_2$)$_q$—OR$_2$, (CH$_2$)$_q$—NR$_5$R$_6$, (CH$_2$)$_q$—CN, C(O)R$_4$, C(O)OR$_4$, (CH$_2$)$_q$—SO$_2$R$_4$, carbocyclic aryl or heterocyclic aryl having 1 to 3 heteroatoms independently selected from N, O and S;

q is an integer selected from 0, 1, 2 and 3;

R$_4$ is H, alkyl of 1 to 4 carbons, carbocyclic aryl or heterocyclic aryl having 1 to 3 heteroatoms independently selected from N, O and S;

R$_5$ and R$_6$ independently are H, alkyl of 1 to 4 carbons, C(O)R$_4$ or benzyl, with the proviso that the claim does not include the compound of the formula

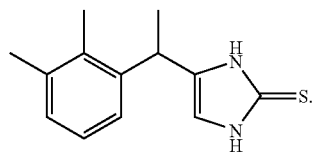

* * * * *

UNITED STATES PATENT AND TRADEMARK OFFICE
CERTIFICATE OF CORRECTION

PATENT NO. : 7,683,089 B1
APPLICATION NO. : 11/232341
DATED : March 23, 2010
INVENTOR(S) : Todd M. Heidelbaugh et al.

It is certified that error appears in the above-identified patent and that said Letters Patent is hereby corrected as shown below:

On the Title page, Item (57), "Abstract", delete "cardivascular" and insert -- cardiovascular --, therefor.

In column 1, line 19, delete "alpha2" and insert -- alpha$_2$ --, therefor.

In column 6, line 14-15, delete "4-(substituted-pheny-methyl)-imidazole-2-thiones" and insert -- 4-(substituted-phenyl-methyl)-imidazole-2-thiones --, therefor.

In column 6, line 66, delete "pheny" and insert -- phenyl --, therefor.

In column 7, line 51, delete "Alpha2" and insert -- Alpha$_2$. --, therefor.

In column 8, line 32, delete "Degeneration," and insert -- Degeneration. --, therefor.

In column 8, line 34, delete "Multi focal" and insert -- Multifocal --, therefor.

In column 8, line 43, delete "Pigement" and insert -- Pigment --, therefor.

In column 9, line 9, delete "Accosiated" and insert -- Associated --, therefor.

In column 9, line 51, delete "erythematosis" and insert -- erythematosus --, therefor.

In column 10, line 39-40, delete "cardivascular" and insert -- cardiovascular --, therefor.

In column 11, line 38-39, delete "phenychlorothionoformate" and insert -- phenylchlorothionoformate --, therefor.

In column 12, line 37, delete "Alpha2" and insert -- Alpha$_2$ --, therefor.

In column 13, line 17, delete "(ie." and insert -- (i.e. --, therefor.

Signed and Sealed this

Twenty-third Day of November, 2010

David J. Kappos
*Director of the United States Patent and Trademark Office*

CERTIFICATE OF CORRECTION (continued)
U.S. Pat. No. 7,683,089 B1

In column 14, line 21, delete "intraperitonealy" and insert -- intraperitoneally --, therefor.

In column 20, line 5, after "4)" insert -- . --.

In column 20, line 20, delete "C1" and insert -- CI --, therefor.